US00PP36514P3

(12) United States Plant Patent
Olesen

(10) Patent No.: US PP36,514 P3
(45) Date of Patent: Mar. 4, 2025

(54) ROSE PLANT NAMED 'Poulpal104'

(50) Latin Name: *Rosa hybrida*
Varietal Denomination: Poulpal104

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,480

(22) Filed: Sep. 8, 2023

(65) Prior Publication Data

US 2024/0107917 P1 Mar. 28, 2024

(30) Foreign Application Priority Data

Sep. 30, 2022 (QZ) ..... PBR 2022/2172

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 6/749; A01H 5/02
See application file for complete search history.

*Primary Examiner* — Keith O. Robinson

(57) ABSTRACT

A new garden rose plant of the Compact Floribunda class which has abundant, red-purple flowers and attractive foliage. This new and distinct variety has shown to be uniform and stable in the resulting generations from asexual propagation.

2 Drawing Sheets

Botanical designation: *Rosa hybrida.*
Variety denomination: 'Poulpal104'.

This application claims priority to Plant Breeder's Rights Application Number 2022/2172, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpal104', originated as a single seedling from the stated cross.

The new variety may be distinguished from its male pollen parent and female seed parent primarily by the following characteristics. The male pollen parent plant has red-purple flowers with 25 petals while the new variety has red-purple flowers with 65 petals. The female seed parent plant has dark red flowers while the new variety has red-purple flowers.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance.

This combination of qualities is not present in previously available commercial cultivars of this type, known to the inventor, and distinguish 'Poulpal104' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpal104' was selected in the spring of 2015 by the inventor as a single plant from the progeny of the aforementioned hybridization.

Asexual reproduction of 'Poulpal104' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpal104' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal104'.

Specifically illustrated in FIG. 1 of the drawings are open flowers viewed from above and the side, flower petals detached revealing reproductive flower parts, sepals detached revealing the receptacle and pedicel, and a flower bud upon opening.

Figure 1:
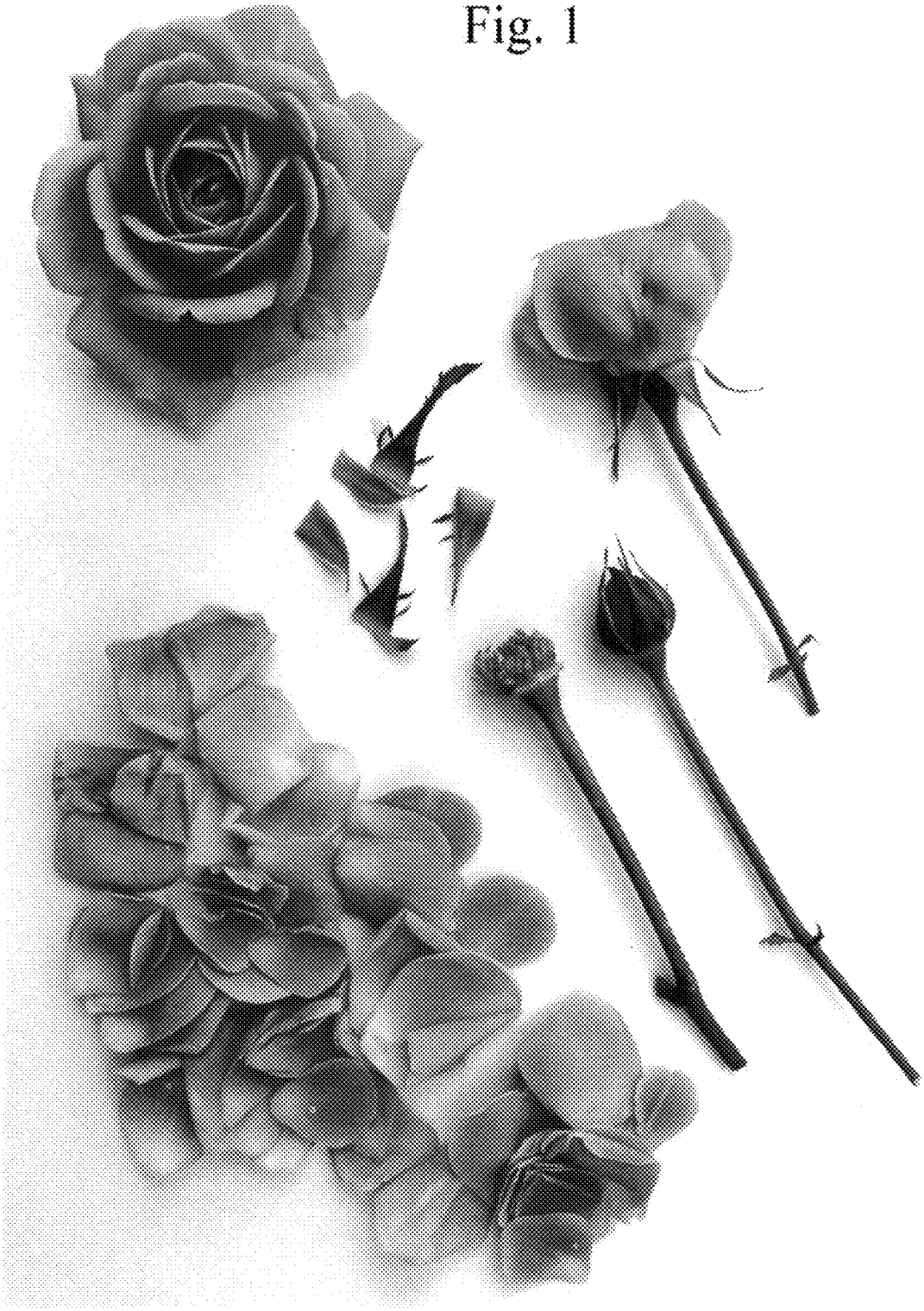
Figure 2:
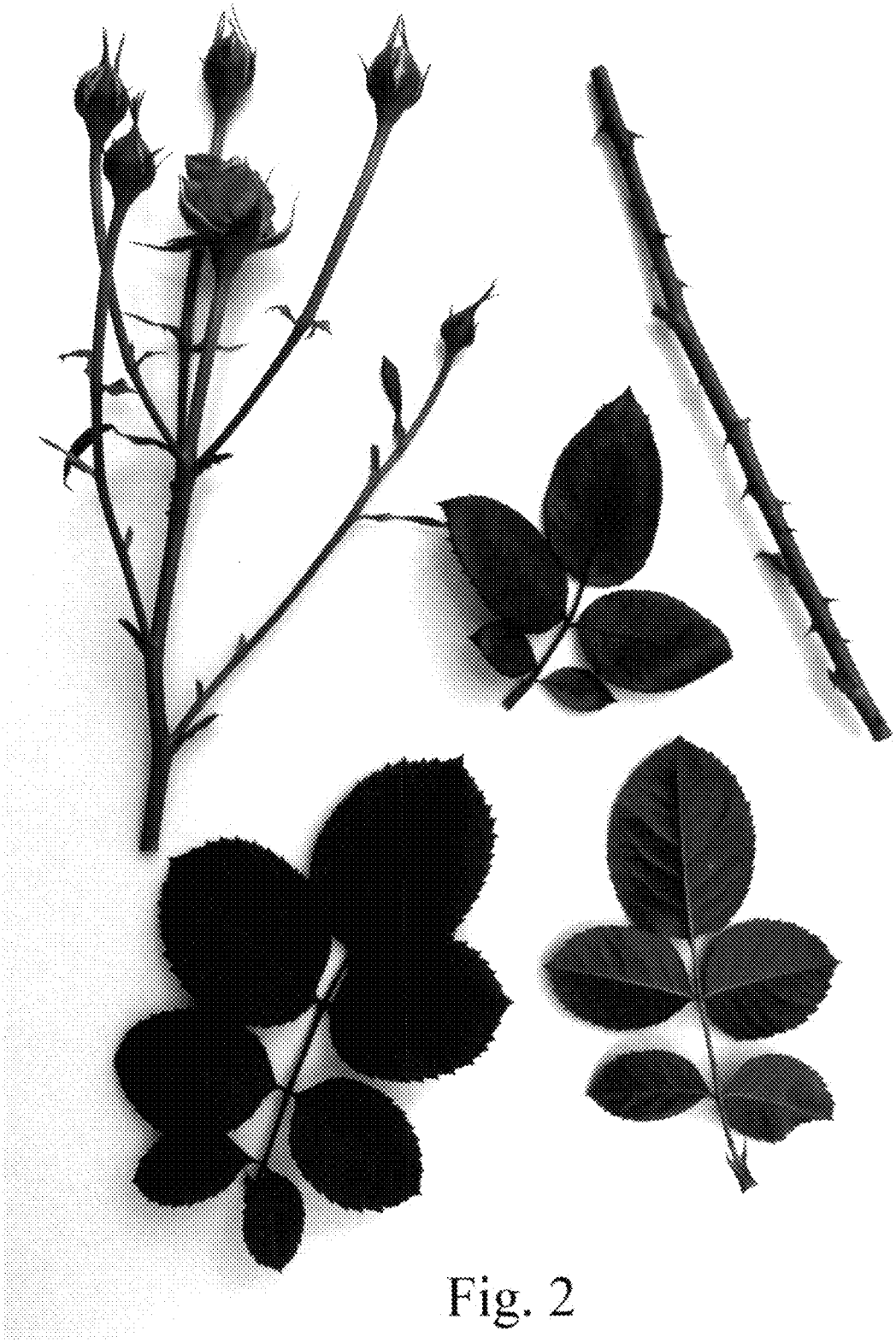

Specifically illustrated in FIG. 2 of the drawings are a cluster of flower buds on a branch, bare stem exhibiting prickles, juvenile and mature leaves. Plants shown are 4 months old.

DETAILED DESCRIPTION OF THE VARIETY

The following is a description of 'Poulpal104', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpal083', U.S. Plant Pat. No. 32,766 are compared to the claimed plant. While 'Poulpal104' has 65 flower petals, 'Poulpal083' has 35 flower petals. The claimed plant has a flower diameter of 80 mm while 'Poulpal083' has a flower diameter of 60 to 70 mm. Open flowers of 'Poulpal104' are generally Red-Purple Group N66D in color while 'Poulpal083' has a general tonality of Red Group 55B.

FLOWER AND FLOWER BUD

Blooming habit: Continuous.

Flower bud:

- *Size*.—Upon opening, 23 mm in length from base of receptacle to end of bud. Bud diameter is 12 mm.
- *Bud form*.—Globose.
- *Bud color*.—As sepals divide petals are Red-Purple Group 63C and Red Group 46C.
- *Sepal inner surface*.—Color: Yellow-Green Group 146D. Surface: Lightly pubescent.
- *Sepal outer surface*.—Color: Yellow-Green Group 144A with intonations of Greyed-Red Group 180B at apex. Texture: Smooth.
- *Sepal shape*.—Apex: Cirrhose. Base: Flat at union with receptacle.
- *Sepal margin*.—Margins have moderate foliaceous appendages on three of the five sepals.
- *Sepal size*.—33 mm long, 10 mm wide.
- *Receptacle*.—Texture: Smooth. Size: 6 mm in height, 6 mm wide. Color: Yellow-Green Group 144A. Shape: Funnel.
- *Pedicel*.—Surface: Smooth. Length: About 63 mm. Diameter: 3 mm on average. Color: Yellow-Green Group 144A. Strength: Strong.
- *Peduncle*.—Length: 15 mm. Diameter: About 4 mm. Color: Yellow-Green Group 144A. Texture: Smooth.

Flower bud development: Flower buds are borne in clusters of 3 to 7 flower buds per stem, forming a corymb.

Flower bloom:

- *Fragrance*.—Strong, citrus perfume.
- *Duration*.—The blooms have a duration on the plant of approximately 21 days. Petals fall cleanly away from plant after flowers have fully matured.
- *Size*.—Flower diameter is 80 mm when open. Flower depth is 35 mm.
- *Flower shape*.—Cupped rosette, very double flower, with many slightly overlapping petals of different sizes.
- *Shape of flower, side view*.—The upper portion is flat. The lower portion is flat concave.

Petalage: Under normal conditions, flowers have about 65 petals.

General tonality of flower: Open flowers are Red-Purple Group N66D. After 10 days, tonality fades to Red-Purple Group 73B and C.

Petal color:

- *Upon opening, outer petals*.—Upper surface: Red-Purple Group N66C at middle zone, N66D marginal zone. Yellow Group 5C at basal zone. Streaks Yellow Group 4D at middle zone. Lower surface: Marginal Red-Purple Group 73B. Middle zone Red Group 43D shades. Yellow Group 4B at basal zone.
- *Upon opening, inner petals*.—Upper surface: Marginal Red-Purple Group 73B. Middle zone streaks Red Group 49B. Basal zone Yellow Group 5B. Lower surface: Basal zone Yellow Group 5C. Middle zone Red Group 48C. Marginal zone Red-Purple Group 65B.
- *After opening, outer and inner petals*.—Upper surface: Red-Purple Group 73B and C with basal petal spot Yellow Group 5D. Lower surface: Purple Group 73D with shades of Purple Group 73B.

Petals:

- *Petal reflex*.—Strong.
- *Margin*.—Small cleft at apex.
- *Shape*.—Broad and elliptic. Apex shape: Rounded. Base shape: Acute.
- *Size*.—40 mm (l)×32 mm (w).
- *Texture*.—Smooth.
- *Thickness*.—Average.

Petaloids:

- *Size*.—15 mm (l) by 12 mm (w).
- *Quantity*.—About 12.
- *Shape*.—Elliptical with an acute base and rounded apices.
- *Color*.—Under Red Group 43C with basal Yellow Group 5B. Upper Red Group 48B with Yellow Group 5B petaloid spot.

Reproductive flower parts:

- *Pollen*.—None observed.
- *Anthers*.—Size: 2 mm in length. Color: Yellow Group 5D. Quantity: 45 on average.
- *Filaments*.—Color: Yellow Group 14A. Length: 5 mm.
- *Pistils*.—Length: 9 mm. Quantity: 32 on average.
- *Stigmas*.—Color: Yellow White 158B.
- *Styles*.—Color: Red Group 45C.
- *Location of stigmas*.—Superior in location relative to the length of the filaments and the height of the anthers.
- *Hips*.—None Observed.

PLANT

Plant growth: Upright. Plants are 52 cm in height, and 32 cm wide.

Stems:

- *Color of juvenile growth*.—Yellow-Green Group 144B.
- *Color of mature growth*.—Yellow-Green Group 144A.
- *Length*.—Canes are about 25 cm from the base of the plant to the flowering portion.
- *Diameter*.—About 4 mm.
- *Internodes*.—On mature canes about 45 mm between nodes.
- *Surface texture*.—Young wood: Smooth. Older wood: Smooth.

Long prickles:

- *Incidence*.—About 12 prickles per 10 cm of stem.
- *Size*.—Average length of prickles on mature stems is 5 mm.

*Shape*.—Upper portion is linear. Lower portion is deep concave.

*Color*.—Juvenile prickles: Yellow-Green Group 144A. Mature prickles: Greyed-Purple Group 183B.

Plant foliage:

*Compound leaf*.—125 mm (l)×95 (w).

*Quantity*.—About 2 leaves per 10 cm of stem on average.

*Leaf bearing angle to the stem*.—45 degrees.

*Color of juvenile foliage*.—Upper side: Yellow-Green Group 144A with intonations of Greyed-Red Group 181A at the margins. Lower side: Yellow-Green Group 144B.

*Color of mature foliage*.—Upper side: Yellow-Green Group 146A. Lower side: Yellow-Green Group 147B.

Plant leaves and leaflets:

*Stipules*.—Size: 7 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 11 mm. Diameter: 2 mm. Upper surface color: Yellow-Green Group 144A. Lower surface color: Yellow-Green Group 144A.

*Rachis*.—Length: Abut 60 mm. Upper surface color: Yellow-Green Group 144A. Lower surface color: Yellow-Green Group 144A.

*Leaflet*.—Quantity: Normally 5 to 7 leaflets. Margins: Serrated. Size: Terminal leaflets are about 56 mm long, and 44 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal104' substantially as described and illustrated herein.

* * * * *